United States Patent [19]

Hirakawa et al.

[11] Patent Number: 5,725,880
[45] Date of Patent: Mar. 10, 1998

[54] PHARMACEUTICAL PREPARATION CONTROLLED TO RELEASE MEDICINAL ACTIVE INGREDIENT AT TARGETED SITE IN INTESTINAL TRACT

[75] Inventors: Yoshiyuki Hirakawa, Kobe; Hiroyuki Yoshino, Suita; Eiji Fukui, Kakogawa; Tami Hanamori, Kobe, all of Japan

[73] Assignee: Tanabe Seiyaku Co., Ltd., Osaka, Japan

[21] Appl. No.: 402,052

[22] Filed: Mar. 10, 1995

[30] Foreign Application Priority Data

Mar. 11, 1994 [JP] Japan ................... 6-040911

[51] Int. Cl.$^6$ ................... A61K 9/32; A61K 9/36; A61K 9/42
[52] U.S. Cl. ................... 424/480; 424/463; 424/476; 424/479; 424/482; 424/494; 424/497; 424/498; 427/2.14
[58] Field of Search ................... 424/474, 475, 424/479, 480, 482, 463, 476, 494, 497, 498

[56] References Cited

U.S. PATENT DOCUMENTS

| | | | |
|---|---|---|---|
| 3,325,365 | 6/1967 | Hotko et al. | 167/82 |
| 3,608,030 | 9/1971 | Tint | 264/113 |
| 5,008,113 | 4/1991 | Kokubo et al. | 424/480 |
| 5,162,117 | 11/1992 | Stupak et al. | 424/475 |
| 5,217,720 | 6/1993 | Sekigawa et al. | 424/480 |

FOREIGN PATENT DOCUMENTS 1456365  11/1976  United Kingdom .

OTHER PUBLICATIONS

Journal of Controlled Release, 2 (1985), pp. 27–38.
Chem. Pharm. Bull., 40(11), pp. 3036–3041 (1992).
Annals New York Academy of Sciences, vol. 618, pp. 428–440 (1991).
Science, vol. 233, pp. 1081–1084 (1986).

Primary Examiner—James M. Spear
Attorney, Agent, or Firm—Birch, Stewart, Kolasch & Birch, LLP

[57] ABSTRACT

A pharmaceutical preparation for oral administration which is controlled to release a medicinal active ingredient at a targeted site in the intestinal tract comprising (a) a core containing a medicinal active ingredient and (b) a press-coated layer comprising an enteric polymer, said layer being provided around the core. In the pharmaceutical preparation of the present invention, the medicinal active ingredient is not released during residence in the stomach and, after discharged from the stomach, until reaching a targeted site in the intestine, and thereafter is quickly released, so that the medicinal active ingredient is efficiently delivered to the targeted site in the intestinal tract.

12 Claims, 2 Drawing Sheets ical Bulletin, 40, 3036-3041 (1992)) and the like, as
PHARMACEUTICAL PREPARATION CONTROLLED TO RELEASE MEDICINAL ACTIVE INGREDIENT AT TARGETED SITE IN INTESTINAL TRACT

BACKGROUND OF THE INVENTION

The present invention relates to a pharmaceutical preparation controlled to release a medicinal active ingredient at a targeted site in the gastrointestinal tract, and more particularly to a pharmaceutical preparation for oral administration from which a medicinal active ingredient can be selectively delivered to any specific site in the intestinal tract.

Selective delivery of a medicinal active ingredient to a specific site in the intestinal tract has been desired in drug therapies, for instance, a local therapy for inflammatory disease in the intestinal tract such as ulcerative colitis or Crohn's disease, or an oral administrative therapy with a medicinal compound of a peptide which is apt to be decomposed chemically or enzymatically in the intestinal tract, with a medicinal compound of which the absorption site is limited, or with other medicinal compound.

In order to efficiently realize the selective delivery of a medicinal active ingredient to a specific site in the intestinal tract, it is necessary to design a pharmaceutical preparation taking into account the physical and physiological environment in the human gastrointestinal tract and the traveling time of the pharmaceutical preparation through the intestinal tract. With respect to the physical and physiological environment in the gastrointestinal tract, it is recognized that the value of pH in the stomach is usually 1.8 to 4.5 in a healthy human and that the value of pH in the intestines is 6.5 to 7.5 and the pH does not essentially differ between the small intestine and the large intestine. According to the results of the widespread research of Davis et al., the residence time of a pharmaceutical preparation in the human stomach is 0.5 to 10 hours and further not only the inter-individual variation thereof is large, but also the residence time is considerably influenced, for example, by feeding, a size of the pharmaceutical preparation to be administered and the like. However, the traveling time of a pharmaceutical preparation through the small intestine is generally recognized to be 3±1 hours and the inter- and intra-individual variation is relatively small (Journal of Controlled Release, 2, 27-38 (1985)).

With respect to a method by which a medicinal active ingredient can be selectively delivered to a specific site in the intestinal tract, hitherto various researches have been done. There have been proposed a pharmaceutical preparation wherein a sustained release pharmaceutical preparation is coated with an enteric coating (Annals of the New York Academy of Science, 618, 428-440 (1991)), a pharmaceutical preparation obtained by utilizing a technique for controlling the starting time of the release (Chemical & Pharmaceutical Bulletin, 40, 3036-3041 (1992)) and the like, as well as pharmaceutical preparations obtained by using known techniques such as an enteric pharmaceutical preparation and a sustained release pharmaceutical preparation.

However, every conventional method has a problem such as insufficient site-selectivity or poor practicality due to peculiarity of the material to be used. For example, in case of using the enteric pharmaceutical preparation, the release of a medicinal active ingredient starts abruptly at the upper small intestine resulting in consumption of almost of the medicinal active ingredient by absorption or decomposition before the medicinal active ingredient reaches the targeted site in the intestine, although the release of the medicinal active ingredient can be effectively suppressed in the stomach. In case of using the sustained release pharmaceutical preparation, a considerable amount of a medicinal active ingredient is released when the pharmaceutical preparation stays in the stomach and passes through the small intestine because the medicinal active ingredient is continuously released.

Further, in order to release a medicinal active ingredient at the large intestine, there has been recently developed a system utilizing the ecosystem of specific microorganisms in the large intestine. For example, in a pharmaceutical preparation wherein a composition containing a medicinal active ingredient is coated with a novel polymer having an azo group, or the composition containing a medicinal active ingredient is dispersed in the new polymer having an azo group to form a matrix type of pharmaceutical preparation (Science, 233, 1081-1084 (1986)), the polymer is decomposed in the large intestine by enterobacteria having azo-reductase activity and the medicinal active ingredient is thereby released at the large intestine. However, for practical use, there are still many problems to be solved, for example, regarding the safety of the polymer itself, the controllability of the decomposition rate thereof, and the like.

An object of the present invention is to solve the above-mentioned problems in the conventional pharmaceutical preparations, and to provide a pharmaceutical preparation for oral administration of high practical use by which a medicinal active ingredient can be effectively released at a targeted site in the intestinal tract.

This and the other objects of the present invention will become apparent from the description hereinafter.

SUMMARY OF THE INVENTION

In accordance with the present invention, there is provided a pharmaceutical preparation for oral administration which is controlled to release a medicinal active ingredient at a targeted site in the intestinal tract comprising (a) a core containing a medicinal active ingredient and (b) a press-coated layer comprising an enteric polymer, said layer being provided around the core.

In the pharmaceutical preparation of the present invention, a lipophilic or hydrophobic substance may be included in the press-coated layer in order to control a dissolution rate of the layer in the intestine.

The pharmaceutical preparation of the present invention has the following characteristics: when the pharmaceutical preparation is orally administered, the release of a medicinal active ingredient does not occur at all during residence of the pharmaceutical preparation in the stomach and, after discharge from the stomach, until the preparation reaches a desirable targeted site in the intestine and thereafter, the release of the ingredient starts rapidly. In case of using a medicinal active ingredient as a drug required to be selectively delivered to a specific site in the intestinal tract, an excellent pharmaceutical preparation having high availability can be provided.

DETAILED DESCRIPTION OF THE INVENTION

Figure 1:
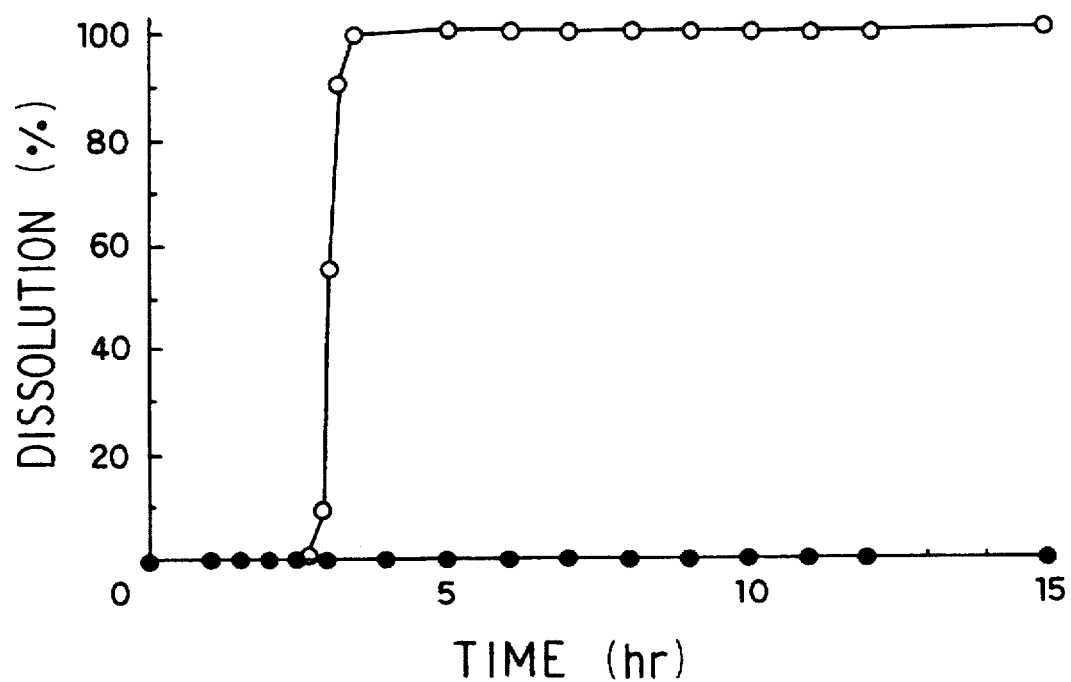
FIG. 1 is a graph showing the result of the dissolution test with the first fluid and the second fluid of the dissolution test in Japanese Pharmacopoeia XII (hereinafter referred to as JPXII) using a pharmaceutical preparation in Example 1.

The present invention has been accomplished based on viewpoints that a press-coated layer comprising an enteric polymer starts to dissolve more slowly in the intestine than a film-coated layer comprising the enteric polymer and that the starting time of dissolution of a medicinal active ingredient can be controlled by varying an amount of the press-coated layer.

In the pharmaceutical preparation of the present invention, the press-coated layer (b) comprising an enteric polymer is capable of suppressing the release of a medicinal active ingredient in the intestine until the pharmaceutical preparation reaches near the desirable targeted site. Namely, during residence of the pharmaceutical preparation in the stomach, the press-coated layer (b) does not dissolve and protects the core (a) so that the release of a medicinal active ingredient can be perfectly supressed, and after discharge of the pharmaceutical preparation from the stomach, the press-coated layer (b) gradually dissolves, and therefore the release of a medicinal active ingredient is substantially suppressed in the intestine until the pharmaceutical preparation reaches near the desirable targeted site.

In order to sufficiently exhibit the above-mentioned capacity in the pharmaceutical preparation of the present invention, it is desirable to determine the time required for dissolution of the press-coated layer (b) in the intestine so that the press-coated layer (b) has sufficient acid resistance and does not dissolve during residence in the stomach, and after discharge from the stomach, the press-coated layer (b) can substantially suppress the release of a medicinal active ingredient until the pharmaceutical preparation reaches near the desirable targeted site in the intestine.

From the above-mentioned viewpoints, it is desirable that the coating amount of the press-coated layer (b) is usually determined so that a medicinal active ingredient is not released in the stomach for a period of about 10 hours which is recognized as the maximum residence time of a pharmaceutical preparation in the stomach, and in case of targeting the upper large intestine, can suppress the release of a medicinal active ingredient in the intestines for about 3±1 hours which is recognized as a general traveling time of a pharmaceutical preparation through the small intestine.

The pharmaceutical preparation of the present invention can be suitably designed so that when a dissolution test is carried out according to the dissolution test (puddle method; 37° C.; 100 rpm; 900 ml of dissolution fluid) of JPXII (refer to Example 1), release of a medicinal active ingredient is substantially suppressed for at least 10 hours in the first fluid (pH 1.2), and the release of the medicinal active ingredient is substantially suppressed for at least about 2 hours in the second fluid (pH 6.8) and thereafter the release of the medicinal active ingredient starts quickly. The time required to start the release of the medicinal active ingredient (hereinafter referred to as "lag-time") in the second fluid is set to meet the desired target-site in the intestinal tract. For example, in case that the pharmaceutical preparation of the present invention is designed to have the lag-time of about 2 hours, about 4 hours or about 7 hours, there can be obtained a pharmaceutical preparation wherein release of a medicinal active ingredient is intended to occur at the lower ileum, the ascending colon or the transverse colon. If the pharmaceutical preparation of the present invention is designed to have the lag-time being longer than about 7 hours, there can be obtained a pharmaceutical preparation wherein release of a medicinal active ingredient is intended to occur at the lower large intestine such as the descending colon or the sigmoid colon.

In the pharmaceutical preparation of the present invention, the core (a) is not particularly limited if only a medicinal active ingredient is included in the core (a). The core (a) may comprise a medicinal active ingredient only. Or if required, various pharmaceutical additives such as an excipient and a disintegrant which are generally used in the art of pharmaceutical preparation, may be included in the core (a) as described below. The form of the core (a) may be a tablet, a granule, a pellet or the like.

The medicinal active ingredient to be included in the above-mentioned core (a) in the present invention is not particularly limited as long as it is orally administerable. Concrete examples of such medicinal active intredient include chemotherapeutic agents, antibiotics, respiratory stimulants, antitussives, expectorants, antimalignanttumor agents, autonomic agents, psychotropic agents, local anesthetics, muscle relaxants, agents affecting digestive organs, antihistamines, toxicopetic agents, hypnotics, sedatives, antiepileptics, antipyretics, analgesics, antiinflammatory agents, cardiotonics, antiarrhythmic agents, diuretics, vasodilators, antilipemic agents, nutrients, tonics, alteratives, anticoagulants, agents for liver disease, hypoglycemics, antihypertensives and the like.

The amount of a medicinal active ingredient to be included in the core (a) is not particularly limited and may be determined according to an effective dose of the medicinal active ingredient to be used, and the like. The amount is preferably about 0.2 to about 100 w/w %, more preferably 0.5 to 50 w/w %, based on a weight of the core (a).

As an enteric polymer used for the press-coated layer (b), any film-formable polymer soluble in an aqueous medium of a pH of not less than 5 and insoluble in an aqueous medium of a pH of less than 5 can be used in the pharmaceutical preparation of the present invention. Examples of the enteric polymer include a cellulose derivative, a polyvinyl derivative, a maleic acid-vinyl compound copolymer, an acrylic copolymer and the like.

Concrete examples of the cellulose derivative include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethylcellulose acetate succinate and the like. Concrete examples of the polyvinyl derivative include polyvinyl alcohol phthalate, polyvinyl butylate phthalate, polyvinyl acetoacetal phthalate and the like. Concrete examples of the maleic acid-vinyl compound copolymer include poly(vinyl acetate, maleic acid anhydride), poly(vinyl butyl ether, maleic acid anhydride), poly(styrene, maleic acid monoester), and the like. Concrete examples of the acrylic copolymer include poly(ethyl acrylate, methacrylic acid), poly(styrene, acrylic acid), poly(methyl acrylate, methacrylic acid, octyl acrylate), poly(methacrylic acid, methyl methacrylate) (e.g. Eudragit L and Eudragit S, each being trade name, available from Röhm Pharma, Germany), and the like.

Among these examples, carboxymethylethylcellulose, hydroxypropylmethylcellulose acetate succinate, hydroxypropylmethylcellulose phthalate and poly(methacrylic acid, methyl methacrylate) (Eudragit L and Endragit S) are preferably used as the enteric polymer, and particularly hydroxypropylmethylcellulose acetate succinate and poly (methacrylic acid, methyl methacrylate) (Eudragit L and Endragit S) are preferable, and more particularly hydroxypropylmethylcellulose acetate succinate is preferable.

The above-mentioned enteric polymers are different in various physical properties such as a dissolution pH (enteric polymers may be somewhat different in a dissolution pH), a molecular weight and a polymerization degree. However, any enteric polymer can be suitably used for preparing a press-coated layer in the pharmaceutical preparation of the present invention by selecting a kind and an amount of the enteric polymer, a compressing pressure of a press-coated layer and the like so that the press-coated layer (b) is capable of suppressing release of a medicinal active ingredient until the pharmaceutical preparation reaches near a desirable targeted site in the intestine, namely can substantially suppress the release of a medicinal active ingredient for any desired period of time (for example, at least 2 hours) in the second fluid of the dissolution test in JPXII.

Thus, with respect to the above-mentioned preparation of the press-coated layer, there is no particular difficulty for a person skilled in the art to select a type or a grade of the enteric polymer and an amount thereof, a compressing pressure and the like so that a medicinal active ingredient can be released at a desired site in the intestinal tract, particularly a targeted site in between the upper small intestine and the lower large intestine.

For instance, a usually used enteric polymer in a commercially available form can be used for tabletting by means of a tabletting machine to obtain a pharmaceutical preparation of the present invention in a form of a tablet.

If an enteric polymer cannot be is used as it is for tabletting because of having a very small particle size (e.g. in a form of a fine powder), the enteric polymer is once transformed to a form of granules having a suitable particle size for tabletting and thereafter the granules are tabletted together with a core tablet. Then, the pharmaceutical preparation of the present invention in a form of a tablet can be obtained. For example, an acrylic enteric polymer is which commercially available under the trade name of Eudragit S or Eudragit L generally has a small particle size, and the acrylic enteric polymer can be used as it is, however, the acrylic enteric polymer can be more suitably used in a form of granules prepared as described above rather than as it is.

The press-coated layer (b) comprising an enteric polymer in the pharmaceutical preparation of the present invention may be a press-coated layer having a multiple layer, which is formed by press-coating a core containing a medicinal active ingredient with one kind of an enteric polymer and providing a further press-coated layer comprising the same or different kind of an enteric polymer around the layer. Additionally, the press-coated layer (b) may be formed by using two or more kinds of enteric polymers in admixture. Each of the above-mentioned press-coated layer having a multiple layer or that comprising two or more kinds of enteric polymers can be suitably used as the press-coated layer (b) in the pharmaceutical preparation of the present invention so long as the press-coated layer (b) is capable of suppressing the release of a medicinal active ingredient until the pharmaceutical preparation reaches near a desirable targeted site in the intestine, namely can substantially suppress the release of a medicinal active ingredient for any desired period of time (for example, at least 2 hours) in the second fluid of the dissolution test in JPXII.

In the press-coated layer (b) in the pharmaceutical preparation of the present invention, a lipophilic or hydrophobic substance (i.e. a substance having lipophilic property or hydrophobic property, hereinafter referred to as "lipophilic/hydrophobic substance") can be suitably included in addition to an enteric polymer in order to control a dissolution rate of the press-coated layer (b), if required. As such lipophilic/hydrophobic substance, a substance which exerts an effect to decrease a dissolution rate of the press-coated layer (b) in aqueous medium at a pH of not less than 5, may be used alone or in admixture of at least two kinds of substances. It is considered that the effect that a dissolution rate of the press-coated layer in aqueous medium of a pH of not less than 5 is decreased, is exerted owing to either a function that the lipophilic/hydrophobic substance prevents the enteric polymer from wetting with water or a mechanism that the lipophilic/hydrophobic substance physically interacts with the enteric polymer to form more tight press-coated layer.

The above-mentioned effect is varied depending on a physical property and an amount of a lipophilic/hydrophobic substance to be used and a kind of the enteric polymer to be used. For instance, generally, the more effect is exerted by using the substance having a lower melting point, and in case of using a metallic salt of a fatty acid as a lipophilic/hydrophobic substance, a multivalent metallic salt thereof exerts more intensive effect than a monovalent metallic salt thereof. Accordingly, the dissolution rate of a press-coated layer can be also controlled by using two or more kinds of the lipophilic/hydrophobic substances.

Examples of the above-mentioned lipophilic/hydrophobic substance suitably used are, for example, a fat and oil, a wax, a hydrocarbon, a higher alcohol, an ester, a higher fatty acid, a metallic salt of a higher fatty acid, other plasticizer and the like.

Concrete examples of the fat and oil include, for example, a vegetable fat and oil such as cacao butter, palm oil, Japan wax or coconut oil; an animal fat and oil such as beef tallow, lard, horse fat or mutton tallow; a hydrogrnated oil obtained from animals such as hydrogrnated fish oil, hydrogrnated whale oil or hydrogensted beef tallow; a hydrogensted oil obtained from plants such as hydrogensted rape seed oil, hydrogenated castor oil, hydrogenated coconut oil or hydrogenated soybean oil; and the like.

Concrete examples of the wax include, for example, a vegetable wax such as carnauba wax, candelilla wax, bayberry wax, ouricury wax or esparto wax, an animal wax such as beeswax, white beeswax, spermaceti, shellac wax or wool wax, and the like.

Concrete examples of the hydrocarbon include, for example, paraffin, vaseline, microcrystalline wax and the like.

As the higher alcohol, a saturated linear alcohol is exemplified, and concrete examples thereof include, for example, a saturated linear monohydric alcohol having 12 to 30 carbon atoms such as lauryl alcohol, tridecyl alcohol, myristyl alcohol, pentadecyl alcohol, cetyl alcohol, heptadecyl alcohol, stearyl alcohol, nonadecyl alcohol, arachic alcohol, behenyl alcohol, carnaubyl alcohol, ceryl alcohol, corianyl alcohol or melissyl alcohol.

Concrete examples of the ester include, for example, an ester of a fatty acid such as myristyl palmitate, stearyl stearate, myristyl myristate or behenyl behenate; a glycerine ester of a fatty acid including a monoglyceride such as glyceryl monolaurate, glyceryl monomyristate, glyceryl monostearate or glyceryl monooleate, a diglyceride such as glyceryl distearate or glyceryl dilaurate, a triglyceride such as glyceryl trilaurate, glyceryl tristearate or glyceryl triacetyl stearate; and the like.

As the higher fatty acid, a saturated linear fatty acid is exemplified, and concrete examples thereof include, for example, a saturated monobasic linear fatty acid having 10 to 32 carbon atoms such as capric acid, undecanoic acid, lauric acid, tridecanoic acid, myristic acid, palmitic acid, margaric acid, stearic acid, nonadecanoic acid, arachic acid, heneicosanoic acid, behenic acid, tricosanoic acid, lignoceric acid, pentacosanoic acid, cerotic acid, heptacosanoic acid, montanic acid, nonacosanoic acid, melissic acid, hentriacontanoic acid or dotriacontanoic acid. Among these higher fatty acids, capric acid and lauric acid are preferable.

As the metallic salt of a higher fatty acid, an alkali metal salt and an alkaline earth metal salt of a higher fatty acid are exemplified, and concrete examples of the metallic salt of a higher fatty acid include a calcium salt, a sodium salt, a potassium salt, a magnesium salt, a barium salt and the like, of the above-mentioned higher fatty acids. Among these metallic salts of a higher fatty acid, calcium stearate and magnesium stearate are preferable.

Concrete examples of the plasticizer include, for example, triacetin, triethyl citrate, acetyl tributyl citrate, acetyl triethyl citrate, diethyl phthalate, polyethyleneglycol, polysorbate and the like. Among these plasticizers, triacetin, triethyl citrate and acetyl triethyl citrate are preferable.

Among such lipophilic/hydrophobic substances, magnesium stearate, calcium stearate, triacetin, lauric acid, capric acid, triethyl citrate, acetyl triethyl citrate and the like are preferable. Particularly, magnesium stearate, calcium stearate, triacetin, lauric acid, capric acid and triethyl citrate are preferable, and more particularly, magnesium stearate, calcium stearate, triacetin and lauric acid are preferable.

The lipophilic/hydrophobic substance may be used alone or in admixture of two or more kinds of the above-mentioned substances.

A preferable combination of the enteric polymer and the lipophilic/hydrophobic substance in the press-coated layer of the pharmaceutical preparation of the present invention is, for example, a combination of a cellulose derivative and a higher fatty acid or a metallic salt thereof, a combination of a cellulose derivative and a plasticizer, and the like. In the more preferable combination, the enteric polymer is hydroxypropylmethylcellulose acetate succinate and the lipophilic/hydrophobic substance is magnesium stearate, calcium stearate, triacetin, lauric acid, or a mixture of magnesium stearate and calcium stearate.

An amount of the lipophilic/hydrophobic substance in the press-coated layer (b) is about 5 to about 100% by weight, preferably 20 to 60% by weight based on a weight of the enteric polymer.

In the core (a) and the press-coated layer (b) of the pharmaceutical preparation of the present invention, various additives such as an excipient, a binder, a disintegrant, a lubricant and an aggregation-preventing agent which are generally used in the field of pharmaceutical preparation may be included, if desired.

Concrete examples of the excipient include a saccharide such as sucrose, lactose, mannitol or glucose, starch, partially pregelatinized starch, crystalline cellulose, calcium phosphate, calcium sulfate, precipitated calcium carbonate, hydrated silicon dioxide and the like. Concrete examples of the binder include an oligosaccharide or a sugar alcohol such as sucrose, glucose, lactose, maltose, sorbitol or mannitol; a polysaccharide such as dextrin, starch, sodium alginate, carrageenan, guar gum, arabic gum or agar; a natural polymer such as tragacanth, gelatin or gluten; a cellulose derivative such as methylcellulose, ethylcellulose, sodium carboxymethylcellulose or hydroxypropylmethylcellulose; a synthetic polymer such as polyvinylpyrrolidone, polyvinylalcohol, polyvinylacetate, a polyethyleneglycol, polyacrylic acid or polymethacrylic acid; and the like. Concrete examples of the disintegrant include calcium carboxymethylcellulose, sodium carboxymethylstarch, corn starch, hydroxypropylstarch, partially pregelatinized starch, low-substituted hydroxypropylcellulose, polyvinylpyrrolidone, calcium cross-linked carboxymethylcellulose and the like. Concrete examples of the lubricant and the aggregation-preventing agent include talc, magnesium stearate, calcium stearate, colloidal silicon dioxide, stearic acid, hydrated silicon dioxide, a wax, a hydrogenated oil, a polyethyleneglycol, sodium benzoate and the like.

The lag-time, the time required until the release of a medicinal active ingredient starts in the intestine or in the second fluid (pH 6.8) of the dissolution test in JPXII, can be controlled by varying a time required for dissolution of the layer (b) as below. For exmaple, if the amount of the press-coated layer (b) is increased (or decreased), the time required for dissolution can be prolonged (or reduced). In case that the coating amount of the press-coated layer (b) is almost constant, the time required for dissolution can be varied by using one or more grades of the enteric polymer having different polymerization degree or substitution degree, in the press-coated layer.

Alternatively, the time required for the dissolution can be also prolonged by including a lipophilic/hydrophobic substance in the press-coated layer (b). Furthermore, if the mount of the lipophilic/hydrophobic substance to be included in the press-coated layer (b) is increased (or decreased), the time required for the dissolution can be prolonged (or reduced). Also, the time required for the dissolution can be varied accordingly to the kind of the lipophilic/hydrophobic substance to be used.

The dosage form of the pharmaceutical preparation of the present invention is preferably a tablet. The size of the pharmaceutical preparation is not particularly limited, however, the diameter thereof is preferably 4 to 16 mm, more preferably 6 to 12 mm.

The form of the core (a) is preferably a tablet. The size of the core (a) is not particularly limited, however, the diameter thereof is preferably 3 to 15 mm, more preferably 5 to 8 mm.

In the pharmaceutical preparation of the present invention, the thickness of the press-coated layer (b) can be selected without any limitation so that the pharmaceutical preparation to be obtained can have a desired lag-time. The thickness of the press-coated layer (b) is usually determined to be 0.4 to 3 mm, preferably 0.5 to 1.5 mm. The coating amount of the press-coated layer (b) corresponding to the above-mentioned thickness, varying according to the size of a core tablet, is usually about 150 to about 600 w/w %, preferably 200 to 400 w/w % based on a weight of the core (a).

The preparation of the core (a) can be carried out according to the usual procedure for the preparation, for example, as described in Remingtons Pharmaceutical Sciences, 17, (Mack Publishing Company, published in 1985). In case of preparing a tablet as a core, for example, the tablet can be obtained by tabletting a medicinal active ingredient alone, or if necessary, admixture with other suitable additives such as an in excipient, a binder and a lubricant which are usually used in the art of pharmaceutical preparation. If necessary, the above-mentioned medicinal active ingredient or mixture is granulated and, if required, sieved before the tabletting process to obtain a granulated particle of the desired range of particle size.

The above-mentioned granulated particle can be prepared according to a usual method such as a dry granulation or a wet granulation. As an example of the granulated particle, for instance, a granule can be prepared by firstly mixing a medicinal active ingredient and a pharmaceutical additive and secondly by granulating the obtained mixture by means of a oscillating granulating machine such as a sieve extruder, a roll extruder, a tornado mill, a screw extruder or alexander machine. A granule can be also prepared by granulating a medicinal active ingredient and a pharmaceutical additive in a form of powder by means of a mixing granulating machine such as a blender granulator or a pin granulator. A granule can be also prepared according to tumbling granulation, i.e. by spraying a binder solution to a medicinal active ingredient and a pharmaceutical additive in a form of powder in a rotating dram or pan, or a granule can be prepared according to fluidizing granulation, i.e. by spraying a binder solution with fluidizing a medicinal active ingredient and a pharmaceutical additive in a form of powder in a fluidized-bed granulator.

Alternatively, the granulated particle can be prepared by coating an inert carrier substance with a medicinal active ingredient and a binder. For instance, granules can be prepared by spray-coating a solution containing a medicinal active ingredient and a binder onto an inert carrier substance. Granulated particles can be prepared according to powder coating, i.e. by firstly mixing an inert carrier substance and a medicinal active ingredient and, if required, other pharmaceutical additive and secondly by coating the obtained mixture with spraying a binder solution.

As the above-mentioned inert carrier substance, for example, a crystalline of a saccharide or inorganic salt such as lactose, cellulose or sodium chloride, a spherical particle and the like can be used. Concrete examples thereof include Avicel SP (trade name, available from Asahi Chemical Industry Co., Ltd., Japan, spherical particle of crystalline cellulose), Nonpareil NP-5 and Nonpareil NP-7 (each being trade name, available from Freund Industrial Co., Ltd., spherical particle of crystalline cellulose and lactose) and the like.

Thus obtained granulated particle can be used for tabletting to prepare a core tablet.

The press-coating to form the press-coated layer (b) around the core (a) is carried out according to a usual method in this field, for instance, a compression molding method such as a press-coating method or a dry coating method, and the like. For example, the press-coated layer can be formed by press-coating the core (a) with an enteric polymer alone, or if necessary, in admixture with a lipophilic/hydrophobic substance and/or other suitable additives such as an excipient, a binder, a lubricant and a fluidizing agent. If necessary, the above-mentioned polymer or mixture is granulated and, if required, sieved according to a usual method before the press-coating process. Then, the press-coated layer is provided on the core. The press-coating can be suitably carried out by means of a press-coating machine or a tabletting machine generally used, under the conditions such that the compressing pressure is, for instance, 200 to 1200 kg/cm$^2$ and the compressing rate is 1 to 20 mm/minute.

An amount of the additives such as an excipient and a disintegrant optionally added in the core (a) and the press-coated layer (b), a concentration of a binder in the binder solution and a solvent to be used can be determined without any limitation so long as it is within a scope based on the usual knowledge of a person skilled in the art of pharmaceutical preparation.

The present invention is more specifically described and explained by means of the following Examples and Experimental Examples. It is to be understood that the present invention is not limited to the Examples, and various changes and modifications may be made in the invention without departing from the spirit and scope thereof.

EXAMPLE 1

Diltiazem hydrochloride (300 g) and corn starch (200 g) were mixed together. The mixture was granulated according to a wet granulation method using a binding solution (180 g) of polyvinylpyrrolidone (trade name: Kollidon 30, available from BASF) (90 g) dissolved in ethanol (90 g). The obtained granules were dried and sieved to obtain granules for tabletting (585 g). A part of thus obtained granules for tabletting (530 g), calcium citrate (120 g), calcium carboxymethylcellulose (trade name: ECG-505, available from Gotoku Chemical Co., Ltd.) (40 g) and magnesium stearate (10 g) were mixed together. The mixture was tabletted by means of a rotary tabletting machine (F-9 Type, made by Kikusui Seisakusho Ltd.) to obtain a plain tablet (a core tablet) having a diameter of 6 mm and a weight of 70 mg.

The obtained plain tablet was press-coated with a mixture of powder of hydroxypropylmethylcellulose acetate succinate (trade name: AQOAT (AS-LF), available from The Shin-etsu Chemical Co., Ltd.), calcium stearate and magnesium stearate (the mixing ratio, by weight (w/w) (hereinafter referred to as "the mixing ratio"), 8:1:1) in a coating amount of 200 mg per tablet by means of a press-coating machine (Correct 18HUK-DC Type, made by Kikusui Seisakusho Ltd.) to obtain a pharmaceutical preparation of the present invention in a form of a press-coated tablet having a diameter of 9 mm and a weight of 270 mg.

With respect to thus obtained pharmaceutical preparation of the present invention, a dissolution test (puddle method) was carried out with the first fluid of the test in JPXII (pH 1.2) and the second fluid of the test in JPXII (pH 6.8) according to the description of the dissolution test in JPXII. The dissolution test was carried out using 900 ml of the dissolution fluid at 37° C. and at the rotation speed of 100 rpm.

The results of the test is shown in FIG. 1. As it is clear from the dissolution pattern of diltiazem hydrochloride being a medicinal active ingredient, in the first fluid, the medicinal active ingredient was not released at all for long time (at least 15 hours), which means that the acid resistance of the pharmaceutical preparation was maintained sufficiently. In the second fluid, the medicinal active ingredient was quickly released after the lag-time of about 3 hours in a pulsatile dissolution pattern.

EXAMPLE 2

The plain tablet containing diltiazem hydrochloride obtained in Example 1 was press-coated with a mixture of powder of hydroxypropylmethylcellulose acetate succinate (trade name: AQOAT (AS-LF), available from The Shin-etsu Chemical Co., Ltd.) and calcium stearate (the mixing ratio, 8:2) in a coating amount of 200 mg per tablet by means of a press-coating machine (Correct 18HUK-DC Type, made by Kikusui Seisakusho Ltd.) to obtain a pharmaceutical preparation of the present invention in a form of a press-coated tablet having a diameter of 9 mm and a weight of 270 mg.

With respect to thus obtained pharmaceutical preparation of the present invention, a dissolution test was carried out with the second fluid of the test in JPXII under the same conditions in Example 1. In the second fluid, the medicinal active ingredient was quickly released after the lag-time of about 10 hours.

EXAMPLE 3

5-Aminosalicylic acid (300 g) and corn starch (200 g) were mixed together. The mixture was granulated according to a wet granulation method using a binding solution (180 g) of polyvinylpyrrolidone (trade name: Kollidon K30, available from BASF) (90 g) dissolved in ethanol (90 g). The obtained granules were dried and sieved to obtain granules for tabletting (585 g). A part of thus obtained granules for tabletting (530 g), calcium citrate (120 g), calcium carboxymethylcellulose (trade name: ECG-505, available from Gotoku Chemical Co., Ltd.) (40 g) and magnesium stearate (10 g) were mixed together. The mixture was tabletted by means of a rotary tabletting machine (F-9 Type, made by Kikusui Seisakusho Ltd.) to obtain a plain tablet (a core tablet) having a diameter of 6 mm and a weight of 70 mg.

The obtained plain tablet was press-coated with a mixture of powder of hydroxypropylmethylcellulose acetate succinate (trade name: AQOAT (AS-LF), available from The Shin-etsu Chemical Co., Ltd.), calcium stearate and magnesium stearate (the mixing ratio, 8:1:1) in a coating amount of 200 mg per tablet by means of a press-coating machine (Correct 18HUK-DC Type, made by Kikusui Seisakusho Ltd.) to obtain a pharmaceutical preparation of the present invention in a form of a press-coated tablet having a diameter of 9 mm and a weight of 270 mg.

With respect to thus obtained pharmaceutical preparation of the present invention, a dissolution test was carried out with the second fluid of the test in JPXII under the same conditions in Example 1. In the second fluid, the medicinal active ingredient was quickly released after the lag-time of about 3 hours.

EXAMPLE 4

The plain tablet containing 5-aminosalicylic acid obtained in Example 3 was press-coated with a mixture of powder of hydroxypropylmethylcellulose acetate succinate (trade name: AQOAT (AS-LF), available from The Shin-etsu Chemical Co., Ltd.), triacetin and hydrated silicon dioxide (the mixing ratio, 8:1:1) in a coating amount of 200 mg per tablet by means of a press-coating machine (Correct 18HUK-DC Type, made by Kikusui Seisakusho Ltd.) to obtain a pharmaceutical preparation of the present invention in a form of a press-coated tablet having a diameter of 9 mm and a weight of 270 mg.

With respect to thus obtained pharmaceutical preparation of the present invention, a dissolution test was carried out with the second fluid of the test in JPXII under the same conditions in Example 1. In the second fluid, the medicinal active ingredient was quickly released after the lag-time of about 3 hours.

EXAMPLE 5

The plain tablet containing 5-aminosalicylic acid obtained in Example 3 was press-coated with a mixture of powder of Eudragit L (trade name, available from Röhm Pharma, poly(methacrylic acid, methyl methacrylate)) and calcium stearate (the mixing ratio, 8:2) in a coating amount of 350 mg per tablet by means of a press-coating machine (Correct 18HUK-DC Type, made by Kikusui Seisakusho Ltd.) to obtain a pharmaceutical preparation of the present invention in a form of a press-coated tablet having a diameter of 11 mm and a weight of 420 mg.

With respect to thus obtained pharmaceutical preparation of the present invention, a dissolution test was carried out with the second fluid of the test in JPXII under the same conditions in Example 1. In the second fluid, the medicinal active ingredient was quickly released after the lag-time of about 4 hours.

EXPERIMENTAL EXAMPLE 1

Figure 2:
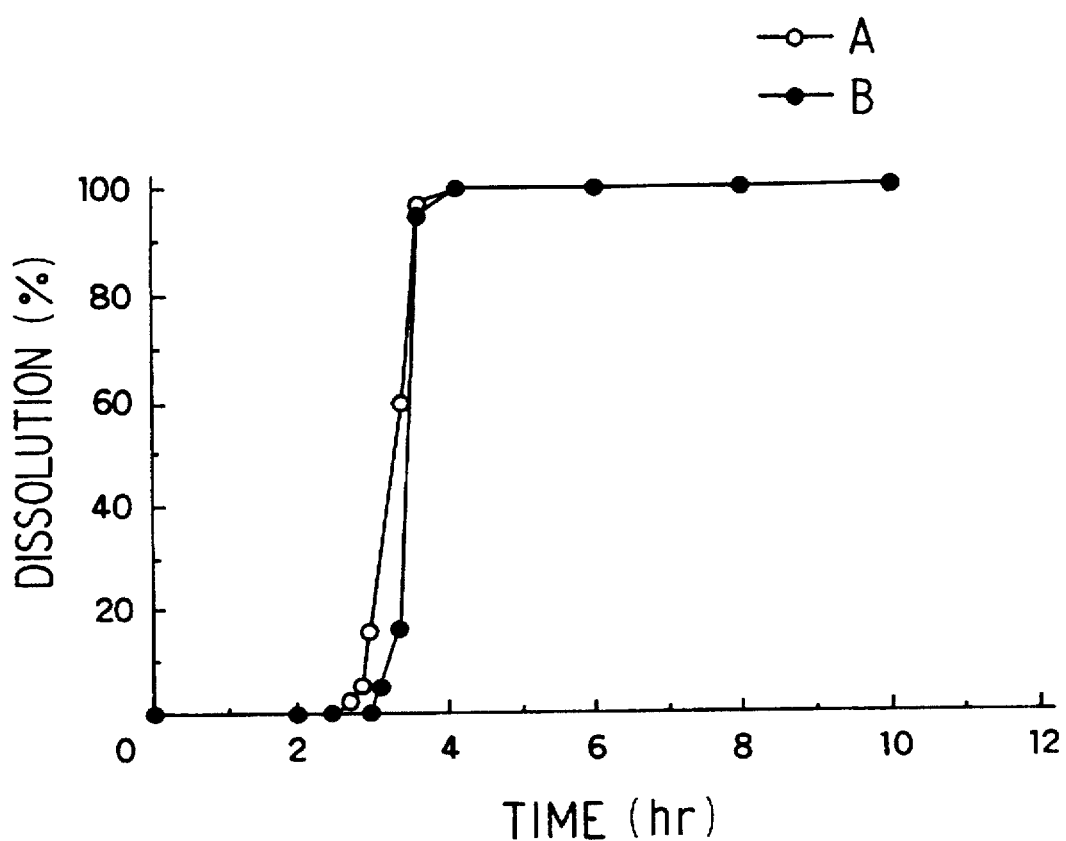
FIG. 2 is a graph showing the result of the dissolution test with the second fluid of the dissolution test in JPXII using a pharmaceutical preparation after immersing in the first fluid of the dissolution test in JPXII for a certain time in Experimental Example 1.

With respect to the pharmaceutical preparation containing diltiazem hydrochloride obtained in Example 1, after immersing in the first fluid of the test in JPXII for a certain time, a dissolution test was carried out with the second fluid of the test in JPXII (the other conditions were the same as in Example 1). The results of the test are shown in FIG. 2. The dissolution patterns A and B represent the results of the dissolution test with the second fluid using the pharmaceutical preparations previously immersed in the first fluid for 0 and 16 hours, respectively.

As it is clear from the dissolution patterns of diltiazem hydrochloride, independent on the immersed time in the first fluid, each dissolution pattern, A and B, was almost the same dissolution pattern of which the lag-time is about 3 hours in the second fluid.

The above-mentioned results suggest that when the pharmaceutical preparation of the present invention is orally administered, without being influenced by the variation of the length of the residence time of the pharmaceutical preparation in the stomach, the eventual release of the medicinal active ingredient starts only at about 3 hours after reaching the small intestine.

In addition to the ingredients used in the Examples, other ingredients can be used in the Examples as set forth in the specification to obtain substantially the same results.

What is claimed is:

1. A pharmaceutical preparation for oral administration which is controlled to release a medicinal active ingredient at a targeted site in the intestinal tract comprising
    (a) a core containing a medicinal active ingredient and
    (b) a press-coated layer comprising an enteric polymer, said layer being provided around said core and said layer being 150–600% by weight based on the weight of said core.

2. The pharmaceutical preparation of claim 1, wherein the enteric polymer is comprised of at least one member selected from the group consisting of carboxymethylethylcellulose, hydroxypropylmethylcellulose acetate succinate, hydroxypropylmethylcellulose phthalate and poly(methacrylic acid, methyl methacrylate).

3. The pharmaceutical preparation of claim 1, which further comprises a lipophilic or hydrophobic substance in the press-coated layer.

4. The pharmaceutical preparation of claim 3, wherein the lipophilic or hydrophobic substance is comprised of at least one member selected from the group consisting of a plasticizer, a higher fatty acid and a metallic salt of a higher fatty acid.

5. The pharmaceutical preparation of claim 3, wherein the lipophilic or hydrophobic substance is comprised of at least one member selected from the group consisting of magnesium stearate, calcium stearate, triacetin, lauric acid, capric acid, triethyl citrate and acetyl triethyl citrate.

6. The pharmaceutical preparation of claim 3, wherein the lipophilic or hydrophobic substance is included in the press-coated layer in an amount of 5 to 100% by weight based on a weight of the enteric polymer.

7. A pharmaceutical preparation for oral administration which is controlled to release a medicinal active ingredient at a targeted site in the intestinal tract comprising (a) a core containing a medicinal active ingredient and (b) a press-coated layer comprising an enteric polymer, said layer being provided around the core, wherein release of a medicinal active ingredient is substantially suppressed for at least 10 hours as determined in the first fluid of a dissolution test according to Japanese Pharmacopoeia XII and the release of the medicinal active ingredient is substantially suppressed for at least 2 hours as determined in the second fluid of the test, said enteric polymer being comprised of at least one member selected from the group consisting of carboxymethylethylcellulose, hydroxypropylmethylcellulose acetate succinate, hydroxypropylmethylcellulose phthalate and poly(methacrylic acid, methyl methacrylate).

8. The pharmaceutical preparation of claim 7, which further comprises a lipophilic or hydrophobic substance in the press-coated layer.

9. The pharmaceutical preparation of claim 8, wherein the lipophilic or hydrophobic substance is comprised of at least one member selected from the group consisting of a plasticizer, a higher fatty acid and a metallic salt of a higher fatty acid.

10. The pharmaceutical preparation of claim 8, wherein the lipophilic or hydrophobic substance is comprised of at least one member selected from the group consisting of magnesium stearate, calcium stearate, triacetin, lauric acid, capric acid, triethyl citrate and acetyl triethyl citrate.

11. The pharmaceutical preparation of claim 8, wherein the lipophilic or hydrophobic substance is included in the press-coated layer in an amount of 5 to 100% by weight based on a weight of the enteric polymer.

12. A pharmaceutical preparation for oral administration which is controlled to release a medicinal active ingredient at a targeted site in the intestinal tract comprising (a) a core containing a medicinal active ingredient and (b) a press-coated layer comprising an enteric polymer, said layer being provided around said core and said layer being 150–600% by weight based on the weight of said core, wherein release of a medicinal active ingredient is substantially suppressed for at least 10 hours as determined in the first fluid of a dissolution test according to Japanese Pharmacopoeia XII and the release of the medicinal active ingredient is substantially suppressed for at least 2 hours as determined in the second fluid of the test.

* * * * *